United States Patent
Davis et al.

(10) Patent No.: US 11,707,576 B2
(45) Date of Patent: Jul. 25, 2023

(54) PLUNGER GASKET WITH REDUCED SURFACE CONTACT

(71) Applicant: Avent, Inc., Alpharetta, GA (US)

(72) Inventors: Benjamin M. Davis, Woodstock, GA (US); David A. Doornbos, Woodstock, GA (US)

(73) Assignee: Avent, Inc., Alpharetta, GA (US)

( * ) Notice: Subject to any disclaimer, the term of this patent is extended or adjusted under 35 U.S.C. 154(b) by 932 days.

(21) Appl. No.: 16/575,469

(22) Filed: Sep. 19, 2019

(65) Prior Publication Data

US 2021/0085885 A1    Mar. 25, 2021

(51) Int. Cl.
| | |
|---|---|
| *A61M 5/315* | (2006.01) |
| *B29D 99/00* | (2010.01) |
| *F16J 15/3236* | (2016.01) |
| *B29L 31/00* | (2006.01) |

(52) U.S. Cl.
CPC ..... *A61M 5/31513* (2013.01); *B29D 99/0053* (2013.01); *F16J 15/3236* (2013.01); *A61M 2207/00* (2013.01); *B29L 2031/7544* (2013.01)

(58) Field of Classification Search
CPC .......... A61M 5/31513; A61M 2207/00; A61M 5/315; A61M 5/31511; A61M 2005/31521; B29D 99/0053; F16J 15/3236; B29L 2031/7544
See application file for complete search history.

(56) References Cited

U.S. PATENT DOCUMENTS

| | | | |
|---|---|---|---|
| 5,795,337 A * | 8/1998 | Grimard | ............ A61M 5/31511 604/222 |
| 9,352,105 B2 | 5/2016 | Hieb et al. | |
| 9,752,003 B2 | 9/2017 | Minagawa | |
| 10,088,050 B2 | 10/2018 | Minagawa | |
| 2007/0219507 A1* | 9/2007 | Dai | .................... A61M 5/31511 604/218 |
| 2009/0047622 A1* | 2/2009 | Leiner | ...................... A61C 5/50 433/90 |
| 2011/0178475 A1* | 7/2011 | Tanaka | ............... A61M 5/31511 604/222 |
| 2014/0081214 A1 | 3/2014 | Hieb et al. | |
| 2017/0296752 A1 | 10/2017 | Masuyama et al. | |
| 2018/0344939 A1 | 12/2018 | Sakashita | |
| 2020/0215269 A1 | 7/2020 | Yotsutsuji | |
| 2020/0338272 A1* | 10/2020 | Yotsutsuji | ......... A61M 5/31515 |

FOREIGN PATENT DOCUMENTS

| | | |
|---|---|---|
| DE | 200 11 336 U1 | 9/2000 |
| EP | 3 677 297 A1 | 7/2020 |

OTHER PUBLICATIONS

International Search Report and Written Opinion for PCT/US2020/047949, dated Oct. 22, 2020, 25 pages.

* cited by examiner

*Primary Examiner* — Lauren P Farrar

(74) *Attorney, Agent, or Firm* — Dority & Manning, P.A.

(57) ABSTRACT

A plunger gasket with reduced surface contact area including a body, a first side defining a first side surface, a second side defining a second side surface, and at least one surface feature projecting outwardly from at least one of the first or second side surfaces. In example embodiments, at least one surface feature projects outwardly from both the first and second side surfaces. By reducing the surface areas of contact between gaskets during manufacture and processing, the incidence of unintentional cohesion may be reduced or eliminated.

24 Claims, 10 Drawing Sheets

PLUNGER GASKET WITH REDUCED SURFACE CONTACT

TECHNICAL FIELD

The present invention relates generally to the field of manufacturing and assembling syringe components, and more particularly to a syringe plunger gasket having one or more surface features provided thereon for efficient post-manufacturing assembly processes and providing further sealing capabilities to the syringe plunger.

BACKGROUND

FIGS. 1-5 show a standard syringe plunger 10 that is configured for use with a syringe barrel B, for example, for tightly engaging an inner wall IW of a cavity of a syringe body B with a substantially fluid tight seal (see FIG. 5). The plunger 10 comprises a body 12 extending between a first end (unshown) and a second end 20. The first end generally comprises a pressure plate, thumb pad or contact face (unshown) that is to be manipulated by a machine or user, and the second end 20 comprises a sealing head 22 comprising a seal or gasket 30 engaged therewith.

Referring to FIG. 2, the gasket 30 comprises a ring or washer-shaped body 31 comprising a central opening 32, an inner surface 33 that is defined by the central opening 32, and an outer peripheral surface 34. The outer peripheral surface 34 can comprise one or more grooves or channels 36 or other surface features as desired. In the depicted example, a channel 36 is formed in the outer peripheral surface 34 and is defined around the entirety of the circumference thereof. In example embodiments, the gasket 30 comprises a first side 40 and a second side 42. The first side 40 defines a first side surface 44 and the second side 42 defines a second side surface 46 (see FIG. 3). Typically, the gasket 30 comprises a uniform thickness and the first and second side surfaces 44, 46 are smooth and configured to be substantially planar with respect to each other. Accordingly, traditional gaskets are typically ring-shaped with substantially smooth and generally flat first and second side surfaces 44, 46.

According to example embodiments, gaskets for use with syringe plungers are typically manufactured in large quantity by injection molding, for example, wherein a multiple cavity mold performs multiple cycles to produce a plurality of gaskets. Typically, gaskets leaving the mold are collected in large quantities and placed in a post-processing treatment bath, for example, a lubrication process so as to permit smooth and sealed movement of the plunger (e.g., sealing head) within the syringe barrel. In some example embodiments, the collected gaskets are placed in a silicone bath, or for example, placed in another bath or lubrication treatment process prior to being individually assembled with the sealing head of a plunger body 12. After being lubricated, the gaskets are individually assembled with the sealing head of a plunger. In some cases, a hopper, carousel or bowl feeder can be used to facilitate automating the assembly of the gasket with the sealing head of the plunger.

Commonly, when the plurality of gaskets 30 are being treated in the lubrication process or silicone bath, one or more gaskets 30 are prone to becoming temporarily connected or stuck to one or more additional gaskets 30 (see FIG. 4). For example, since the first and second side surfaces 44, 46 are substantially smooth, uniform and planar, the presence of the lubrication thereon unintentionally acts as a bonding agent or a cohesive force. Thus, the cohesive force between a first or second side surface of one gasket with a first or second side of another gasket is substantially greater than any other force present, thereby causing a plurality of gaskets 30 (e.g., two or more) to become connected together, for example, so that they are generally stacked or aligned in a concentric manner (see FIG. 4).

But most hoppers, carousels or bowl feeders, for example, which are typically used to automate the assembly of the gasket with the sealing head of the plunger, do not function properly when the gaskets become stuck together. For example, in most cases during assembly when a plurality of gaskets unintentionally connect or stick together, the entire assembly line must be temporarily shut down and the gaskets must be separated. Shutting down the assembly line and pausing manufacturing can cause headaches, time delays and increase costs.

Furthermore, in some cases, even with the plunger and gasket assembled with the sealing head, some syringes are prone to evaporation. For example, according to some cases, some syringes such as syringes used for storage are prone to permit at least some air or liquid contents contained within the syringe barrel to evaporate or escape through the sealing head of the plunger that is sealingly engaged with the inner wall of the syringe barrel.

Accordingly, it can be seen that needs exist for improvements to plunger gaskets, their manufacture and assembly thereof, and their sealability within the syringe barrel. It is to the provision of a plunger gasket with reduced surface contact meeting these and other needs that the present invention is primarily directed.

SUMMARY

In example embodiments, the present invention provides a plunger gasket or seal ring comprising at least one surface feature provided on one or both side surfaces thereof. In example embodiments, at least a portion of each side surface of the plunger gasket comprises a raised protrusion. In example embodiments, the at least one protrusion is continuous so as to form a connected loop around one or both side surfaces of the gasket. In another example embodiment, the at least one protrusion is discontinuous.

In one aspect, the present invention relates to a plunger gasket with reduced surface contact including a body, a first side defining a first side surface, a second side defining a second side surface, and at least one raised surface feature projecting outwardly from at least one of the first or second side surfaces. The body includes a central opening, an inner surface defined by the central opening and an outer peripheral surface defined at an outermost portion of the body. The first side surface is defined on the first side of the body and a second side surface is defined on the second side of the body. The first and second side surfaces being generally smooth and offset relative to each other so as define a first thickness therebetween, wherein the first side surface comprises a first side surface area and the second side surface comprises a second side surface area. The at least one raised surface feature projects outwardly from at least one of the first or second side surfaces. The at least one protrusion or surface feature including an outermost contact surface defining a raised surface area that is substantially less than the first and second side surface areas of the first and second side surfaces.

In example embodiments, the at least one surface feature includes at least one rib projecting outwardly from both the first and second side surfaces, each of the at least one ribs including proximal ends connected to the first and second side surfaces of the body, and distal ends generally outwardly offset from the first ends, wherein the projections extend outwardly from the respective first and second side surfaces to their respective outermost contact surfaces.

In example embodiments, the plunger gasket further includes side surfaces generally defined on either side of the outermost contact surface from the first and second ends of the projections. In example embodiments, a thickness of between about 0.20 mm-0.30 mm is defined between the first and second ends of the rib-like projections. In example embodiments, a width of between about 0.25 mm-0.50 mm is defined between the side surfaces. In example embodiments, the rib-like projections extend along a spiraled path. In example embodiments, the spiraled path of one of the projections extends in a clockwise direction and wherein the spiraled path of the other of the projections extends in a counter-clockwise direction.

In example embodiments, the spiraled path is discontinuous and comprises first and second surface feature ends, the spiraled path completing at least one revolution such that at least some overlap is provided between the first and second ends. In example embodiments, the at least one rib includes an undulating profile of alternating peaks and valleys extending along a circular path, the circular path being continuous. In example embodiments, the present invention includes the gasket in combination with a plunger body having a sealing head, the sealing head including a receiving channel defined between spaced-apart inner surfaces, the spaced-apart inner surfaces configured for sealingly engaging the outermost contact surfaces of the at least one rib. In example embodiments, the outermost contact surface of the at least one surface feature includes an area that is between $1/16^{th}$-$1/256^{th}$ the area of one of the first or second side surfaces. In example embodiments, the gasket includes an outer diameter of between about 4.5 mm-30 mm, an inner diameter of between about 2 mm-25 mm, and a thickness of between about 0.75 mm-10.5 mm, and wherein the at least one surface feature defines a width of between about 0.125 mm-10 mm and a thickness of between about 0.10 mm-0.85 mm.

In another aspect, the invention relates to a gasket for automated assembly with a sealing head of a plunger body including a generally cylindrical-shaped body, a first side defining a first side surface, a second side defining a second side surface, and at least one projection outwardly extending from the first and second side surfaces. The generally cylindrical-shaped body having an outer diameter and a central opening defining an inner diameter. In example embodiments, a contact surface is defined at outermost portions of the at least one projection of the first and second side surfaces.

In example embodiments, the first and second side surfaces each define a substantially similar surface area, and wherein the contact surface of each of the outermost portions of the at least one projection includes a contact surface area, the contact surface area being substantially less than the surface areas of the first and second side surfaces. In example embodiments, the at least one projection generally includes a rectangular cross section defining a first end connected with the first and second side surfaces, and a second end outwardly spaced from the first end and defining the contact surface. In example embodiments, the at least one projection extending from the first and second side surfaces substantially reduces the surface area available for contact between surfaces of two or more grouped-together gaskets such that unintentional cohesion of the two or more gaskets is prevented or at least substantially reduced.

In still another aspect, the invention relates to method of making and assembling multiple syringe plungers including providing a plurality of plunger bodies, each plunger body having a first end and a second end, the first end having a pressure plate and the second end having a sealing head, the sealing head having a channel bound by inner surfaces; providing a plurality of gaskets for automated assembly with the channel of the sealing head, each gasket having a circular body having an outer diameter, a central opening defining an inner diameter, a first side defining a first side surface, a second side defining a second side surface, a thickness, and at least one projection outwardly extending from the first and second side surfaces, wherein a contact surface is defined at outermost portions of the at least one projection of the first and second side surfaces; lubricating the plurality of gaskets in a silicone bath; containing the plurality of lubricated gaskets within an automated assembly mechanism, the plurality of lubricated gaskets generally freely positioned and oriented within the automated assembly mechanism, wherein the automated assembly mechanism provides for feeding each of the plurality of lubricated gaskets to be assembled with individual plunger bodies, wherein the at least one projection and contact surface thereof of the first and second side surfaces substantially reduces a contact surface area of each of the plurality of lubricated gaskets such that cohesion between one or more of the lubricated gaskets is eliminated or at least substantially reduced.

In example embodiments, the method further includes attaching a lubricated gasket on the sealing head of the plunger body to form an assembled plunger, wherein the lubricated gasket is configured for fitting within the channel of the sealing head. In example embodiments, the method further includes assembling the assembled plunger with a syringe body. In example embodiments, the contact surface of the at least one projection of the first and second side surfaces is configured for sealing against the inner surfaces of the channel of the sealing head.

In yet another aspect, the present invention relates to a method of fabricating at least one gasket including providing a mold comprising one or more cavities; and injecting a material within the one or more cavities of the mold to form one or more gaskets, each of the one or more gaskets including a gasket body having a first side and a second side, a first side surface provided on the first side and a second side surface provided on the second side, and at least one raised surface feature formed on the first and second side surfaces.

In example embodiments, the method further includes lubricating the one or more gaskets. In example embodiments, the method further includes containing the one or more lubricated gaskets within an automated assembly mechanism, the one or more lubricated gaskets generally freely positioned and oriented within the automated assembly mechanism, wherein the at least one raised surface feature of the first and second side surfaces substantially reduces a contact surface area of each of the plurality of lubricated gaskets such that cohesion between one or more of the lubricated gaskets is substantially reduced. In example embodiments, the method further includes installing each of the one or more gaskets on respective syringe plungers.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

DETAILED DESCRIPTION OF EXAMPLE EMBODIMENTS

Figure 1:
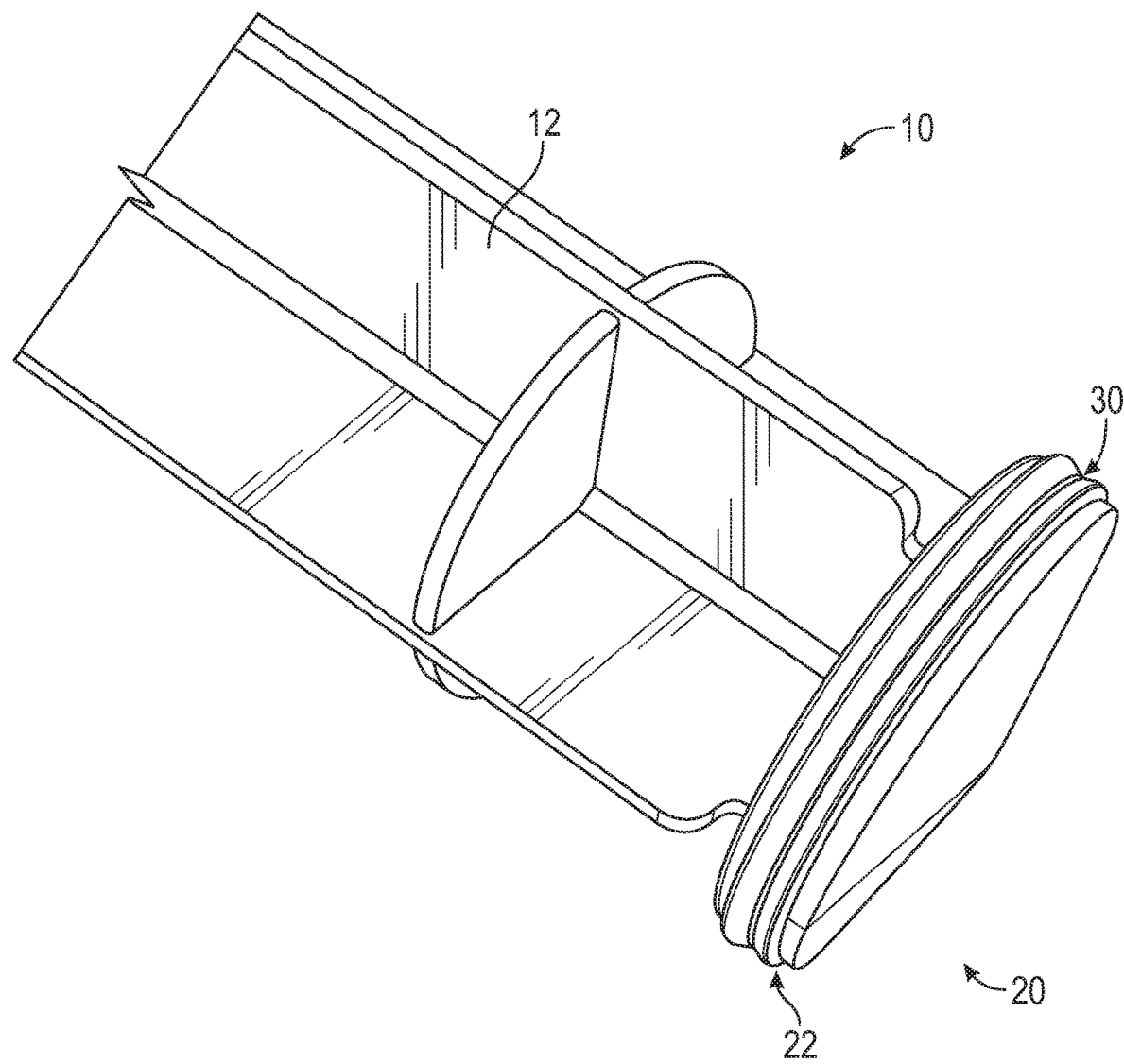
FIG. 1 is a detailed perspective view of a typical plunger and sealing head for use with a traditional syringe barrel.
Figure 2:
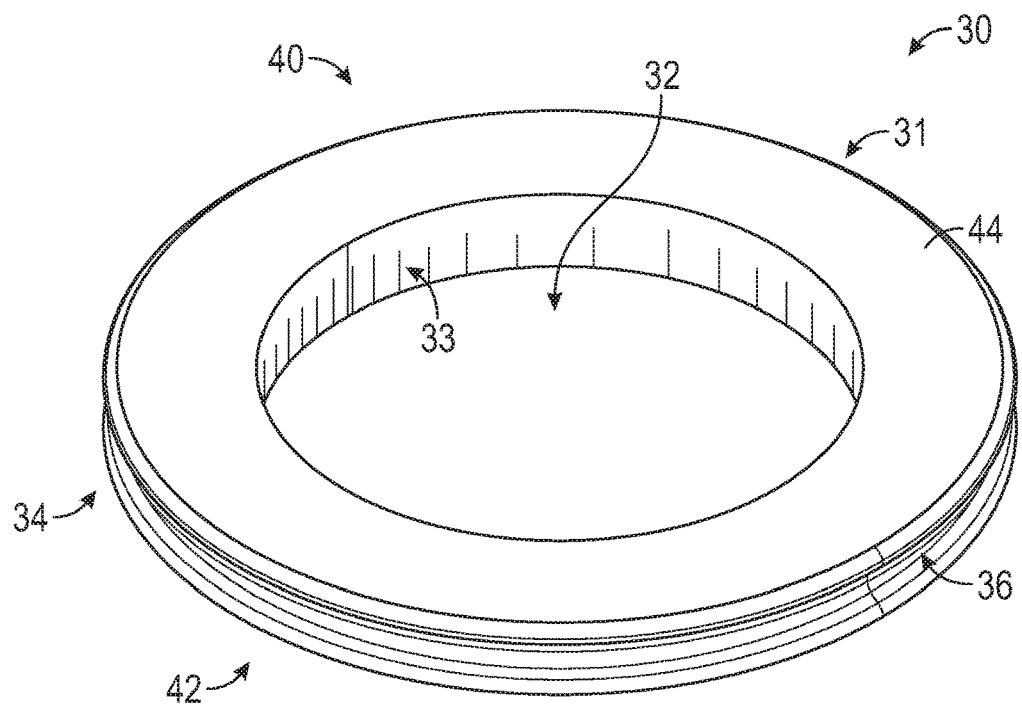
FIG. 2 is a perspective view of a typical gasket seal for use with the sealing head of the plunger of FIG. 1.
Figure 3:
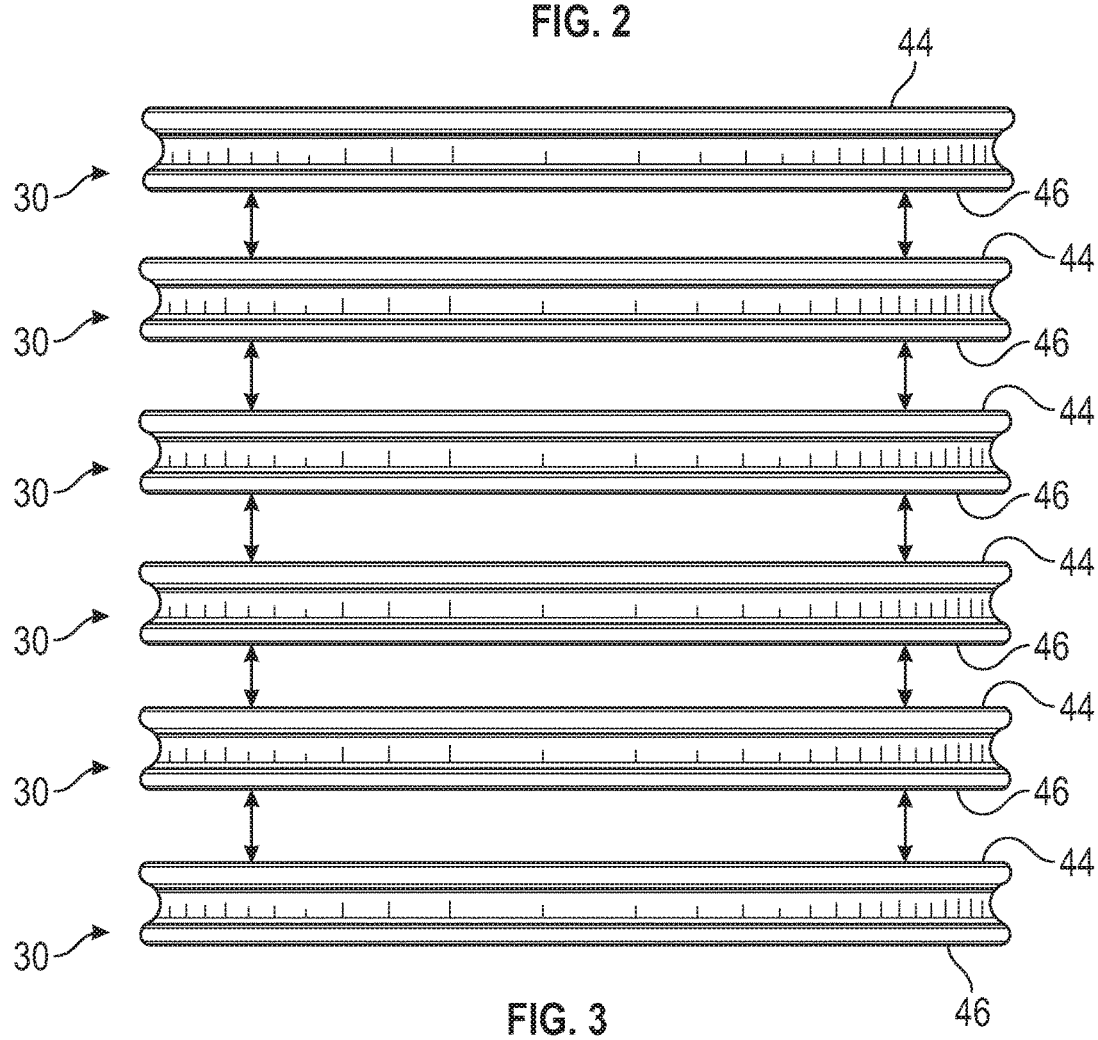
FIG. 3 is a side view of a plurality of typical gasket seals aligned and generally spaced apart from each other.
Figure 4:
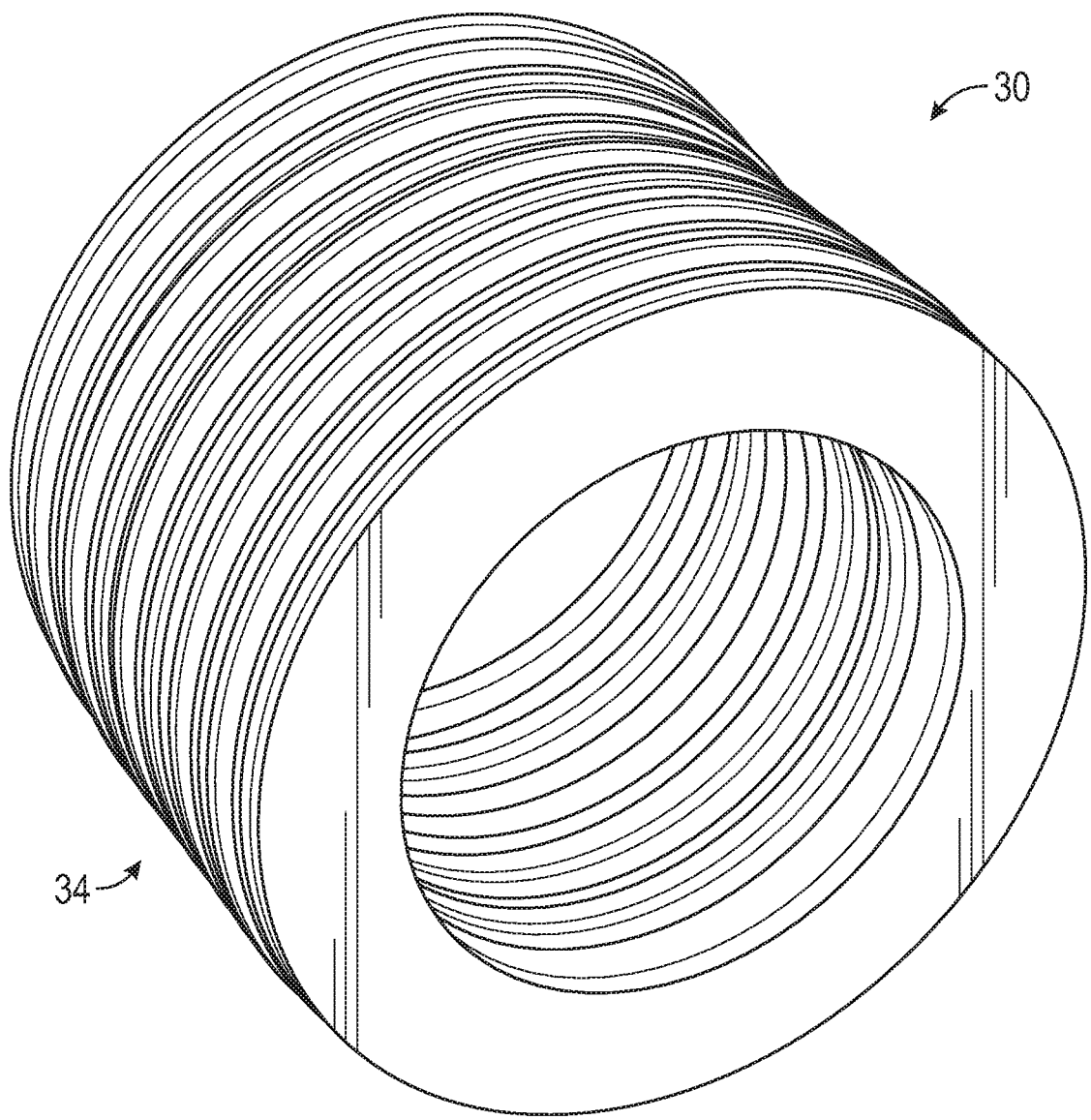
FIG. 4 shows the plurality of typical gasket seals substantially aligned and removably connected together.

The present invention may be understood more readily by reference to the following detailed description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 6-14 show a plurality of sealing components or gaskets 130 according to example embodiments of the present invention. In example embodiments, at least one side surface of the gasket preferably comprises at least one protrusion or raised surface portion. In the depicted example embodiments, both side surfaces of the gasket comprise a protrusion or raised surface portion.

In example embodiments, the gasket or seal ring 130 is generally similar to the gasket 30 as described above. For example, the gasket 130 similarly comprises an annular ring or washer-shaped body comprising a central opening 132, an inner surface 133 that is defined by the central opening 132, and an outer peripheral surface 134. In example embodiments, the outer peripheral surface 134 can comprise one or more grooves or channels or other surface features as desired, for example, a central channel formed in the outer peripheral surface 134 and is defined around the entirety of the circumference thereof. In example embodiments, the gasket 130 comprises a first side 140 and a second side 142. The first side 140 defines a first side surface 144 and the second side 142 defines a second side surface 146.

According to example embodiments of the present invention, at least one protrusion or surface feature is provided on at least one side surface of the gasket or sealing ring 130. According to a preferred example embodiment of the present invention, at least one protrusion or surface feature is provided on both the first and second side surfaces 144, 146 of the gasket. In example embodiments, the at least one protrusion or surface feature can be continuous or discontinuous, or for example, the at least one protrusion or surface feature can be a combination of continuous and discontinuous features.

Figure 6:
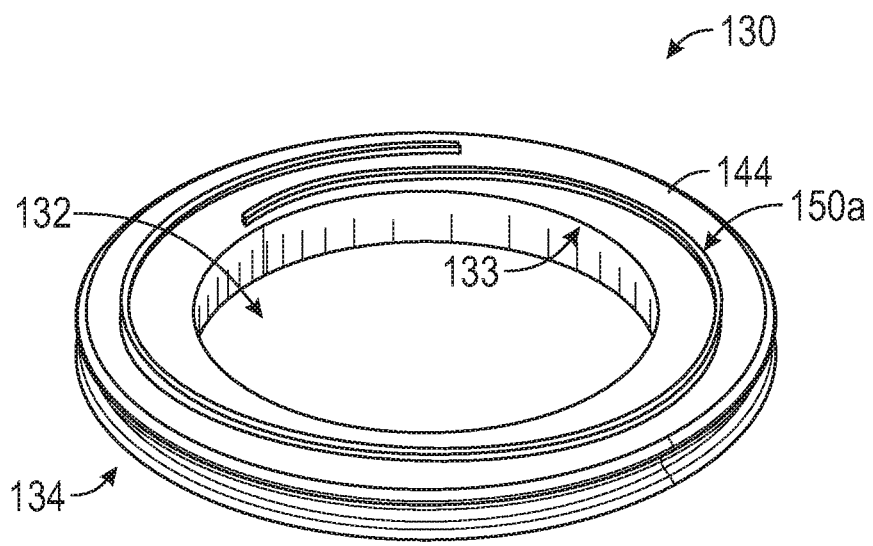
FIG. 6 is a perspective view of a first side of a gasket or seal ring according to an example embodiment of the present invention, the first side of the gasket comprising surface features.
Figure 7:
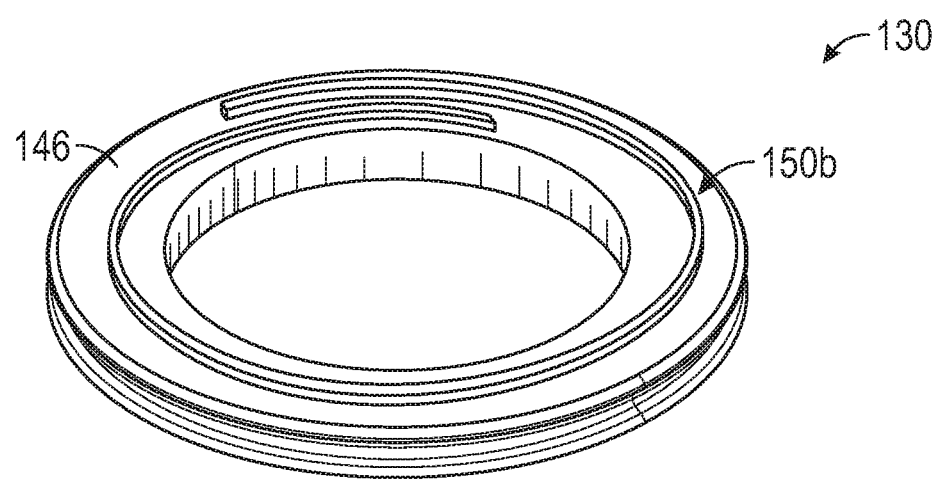
FIG. 7 is a perspective view of a second side of the gasket of FIG. 6, the second side of the gasket comprising surface features.
Figure 8:
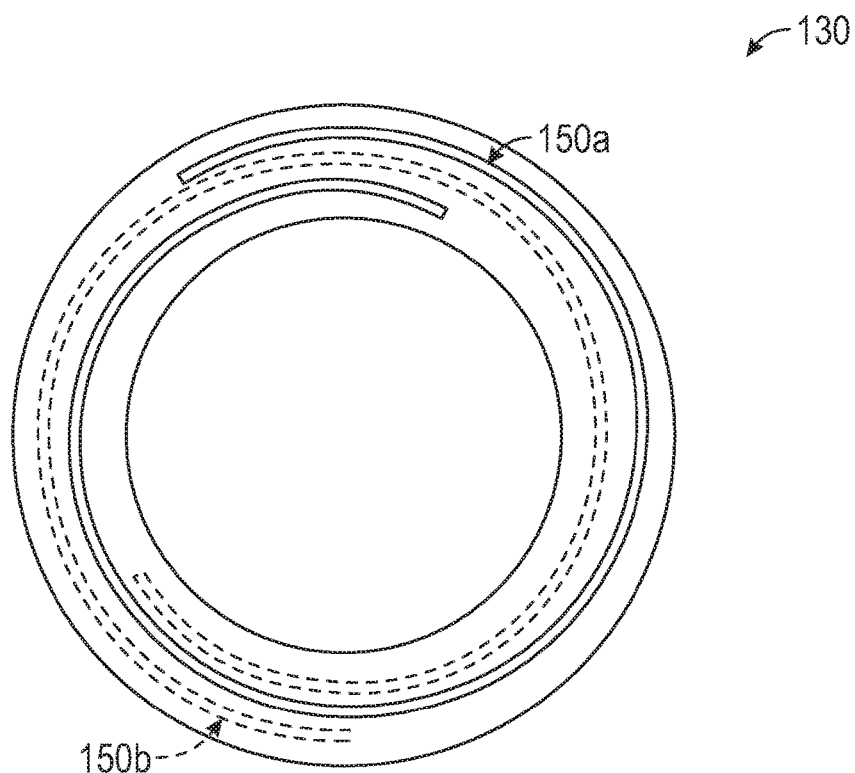
FIG. 8 is a plan view of the first side of the gasket of FIG. 6 and showing the surface features of the first and second sides of FIGS. 6-7.

For example, as depicted in FIGS. 6-8, the first side surface 144 comprises a first protrusion or raised surface feature 150a and the second side surface 146 comprises a second protrusion or raised surface feature 150b. In example embodiments, the surface features 150a, 150b define generally rib-like projections that extend along a helical or spiraled path. As such, according to one example embodiment, the surface features 150a, 150b are discontinuous. As depicted in FIG. 6, the surface feature 150a, for example, which is integrally formed with the first side surface 144 of the gasket 130, extends along a spiraled path in a counterclockwise direction, from a first surface feature end that is generally inwardly-spaced from the outer peripheral surface 134 to a second surface feature end that is generally outwardly-spaced from an inner surface 133 that is defined by the central opening 132. In example embodiments, the surface feature 150a preferably completes at least one revolution such that at least some overlap is provided between the first and second surface feature ends of the surface feature 150a.

In a similar manner, surface feature 150b of the second side surface 146 defines a rib-like projection that extends along a spiraled path and being integrally formed with the second side surface 146. As depicted in FIG. 7, the surface feature 150b, which is integrally formed with the second side surface 146 of the gasket 130, extends along a spiral path in a clock-wise direction, from a first surface feature end that is generally inwardly-spaced from the outer peripheral surface 134 to a second surface feature end that is generally outwardly-spaced from an inner surface 133 that is defined by the central opening 132. In example embodiments, the surface feature 150a preferably completes at least one revolution such that at least some overlap is provided between the first and second surface feature ends of the surface feature 150a. FIG. 8 shows a plan view of the gasket 130 depicting the configuration of how the surface features 150a, 150b are arranged relative to each other. According to example embodiments, the spiral path of the rib-like projections is configured such that a midpoint portion of one of the surface features 150a, 150b is generally positioned between the overlapping ends of the other surface feature 150a, 150b. For example, as depicted in FIG. 8, a midpoint portion of the surface feature 150a is generally oriented and positioned so as to be generally between the overlapped ends of the surface feature 150b. As such, a midpoint portion of the surface feature 150b is generally oriented and positioned so as to be generally between the overlapped ends of the surface feature 150a.

Figure 9:
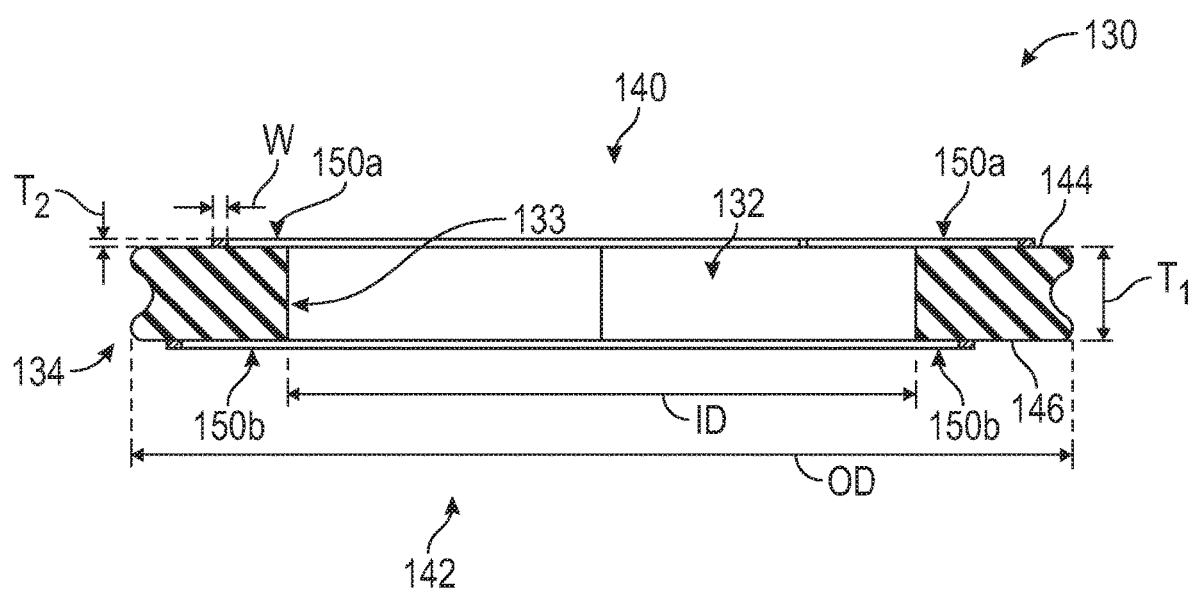
FIG. 9 is a perspective view of a first side of a gasket according to another example embodiment of the present invention, the first side comprising surface features.

FIG. 9 shows a cross sectional view of the gasket 130 according to an example embodiment of the present invention. As depicted, the gasket 130 comprises a thickness T1, an outer diameter OD and an inner diameter ID. In example embodiments, the surface features 150a, 150b of the first and second side surfaces 144, 146 comprise a width W and project above their respective side surface 144, 146 a height or thickness T2. According to the depicted example embodiment, the thickness T1 is about 2.50 mm, the outer diameter OD is about 26.50 mm, the inner diameter ID is about 18.00 mm, the width W is about 0.50 mm and the thickness T2 is 0.25 mm. According to one example embodiment, the gasket 130 and dimensions as described above are generally configured for a 60 mL syringe barrel.

Figure 16:
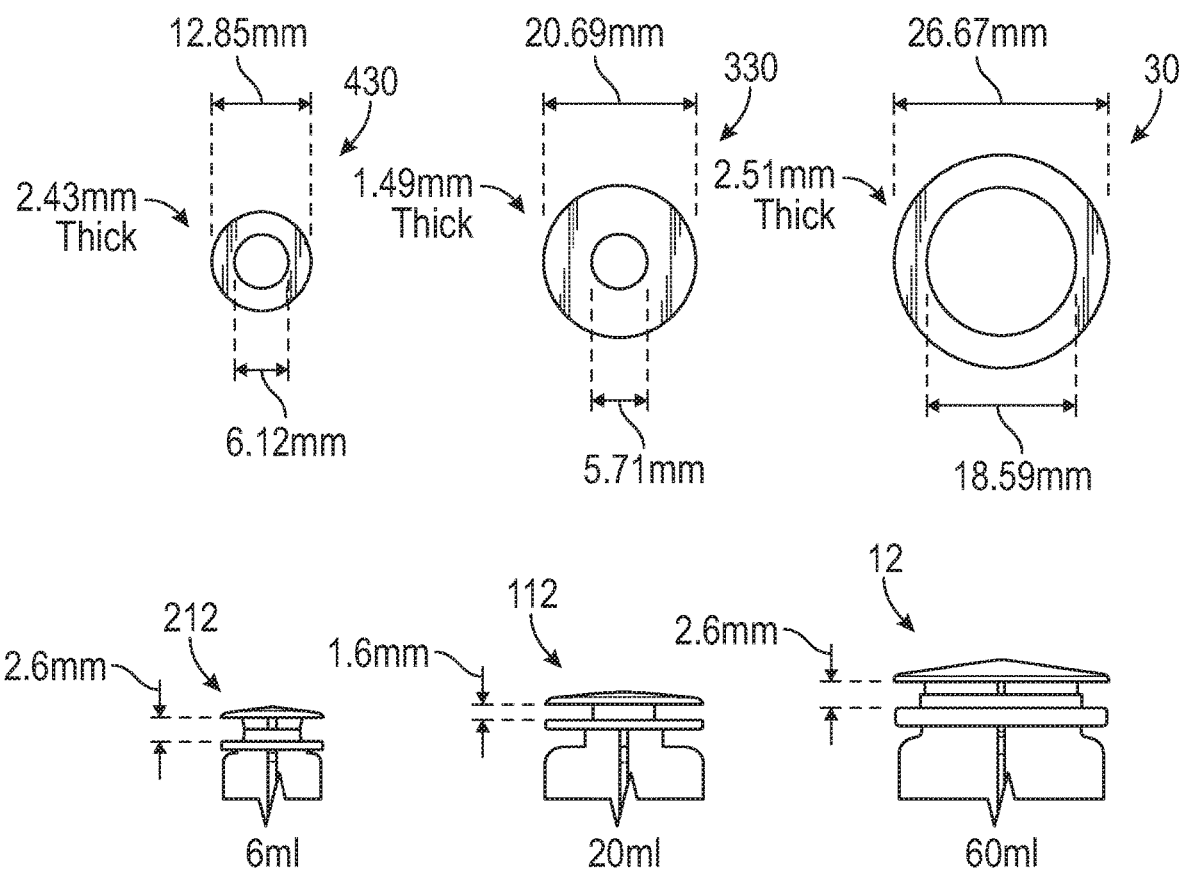
FIG. 16 is a plan view of a plurality of disassembled plungers showing the gaskets being disconnected from the sealing heads thereof according to an example embodiment of the present invention.

For example, as depicted in FIG. 16, a side view of the 60 mL sealing head of the plunger body 12 defines a channel having a width of about 2.60 mm. In alternate example embodiments, the width W and thickness T2 of the surface features 150a, 150b can preferably be sized as desired. According to alternate example embodiments, the width W can be between about 0.125 mm-10 mm, or for example, the width W can be equivalent to the difference between the outer diameter and inner diameter of the gasket (e.g., OD−ID=W). Similarly, according to alternate example embodiments, the thickness T2 can preferably be between about 0.10 mm-0.85 mm, or for example, generally between about 0.20 mm-0.35 mm according to some example embodiments.

According to the depicted example embodiment of FIG. 9, the surface features 150a, 150b are preferably configured to comprise a uniform thickness T2. However, according to alternate example embodiments, the one or more surface features can comprise a thickness T2 that varies, or for example, can comprise at least one portion thereof comprising a minimum thickness and can comprise another portion having a maximum thickness. According to another example embodiment, the thickness T2 can undulate in a wave-like, zig-zag or random pattern, or for example a combination of two or more patterns, so as to further reduce the contact area. Thus, according to some example embodiments, an outermost surface of a surface feature provided on at least one side surface of the gasket can comprise a thickness that varies, for example such that an outermost surface thereof is closer to the side surface at certain portions and further away from the side surface at other portions.

According to alternate example embodiments, preferably the plunger body, sealing head (and channel thereof) and gasket can be sized as desired so as to provide for sealingly engaging the inner wall IW of the syringe barrel B, and thus permit proper functionality of the syringe. Still referring to FIG. 16, a 6 mL, 20 mL and 60 mL plunger body and corresponding traditional gaskets (e.g., without surface features) are depicted to illustrate some of the various sizes capable of being altered to comprise the protrusions or surface features projecting from the first and second side surfaces. According to some example embodiments, the 20 mL plunger body 112 comprises a sealing head defining a channel having a width of about 1.6 mm. The 6 mL plunger body 212 comprises a sealing head defining a channel having a width of about 2.6 mm. And as described above, the channel of the sealing head of the plunger body 12 comprises a width of about 2.60 mm. In alternate example embodiments, plunger bodies dimensioned for other syringe sizes (e.g., 0.5 mL-120 mL) can comprise sealing heads defining channels having widths between about 0.5 mm-8.5 mm.

And depicted above the plunger bodies are the corresponding gaskets (e.g., traditional gaskets without surface features) and example dimensions thereof. For example, the 20 mL gasket 330 comprises an outer diameter of about 20.50 mm, for example about 20.69 mm according to one example embodiment, an inner diameter of about 5.65 mm, for example about 5.71 mm according to one example embodiment, and a thickness of about 1.35 mm, for example about 1.49 mm according to one example embodiment. The 6 mL gasket comprises an outer diameter of about 12.75 mm, for example about 12.85 mm according to one example embodiment, an inner diameter of about 6.00 mm, for example about 6.12 mm according to one example embodiment, and a thickness of about 2.35 mm, for example about 2.43 mm according to one example embodiment. And as described above, the gasket 30 (e.g., 60 mL) comprises an outer diameter of about 26.50 mm, for example about 26.67 mm according to one example embodiment, an inner diameter of about 18.00 mm, for example about 18.59 mm according to one example embodiment, and a thickness of about 2.50 mm, for example about 2.51 mm according to one example embodiment. According to other example embodiments, the gasket can be sized as desired, for example, comprising an outer diameter of between about 4.5 mm-30 mm, an inner diameter of between about 2.0 mm-25 mm, and a thickness of between about 0.75 mm-10.5 mm.

Figure 5:
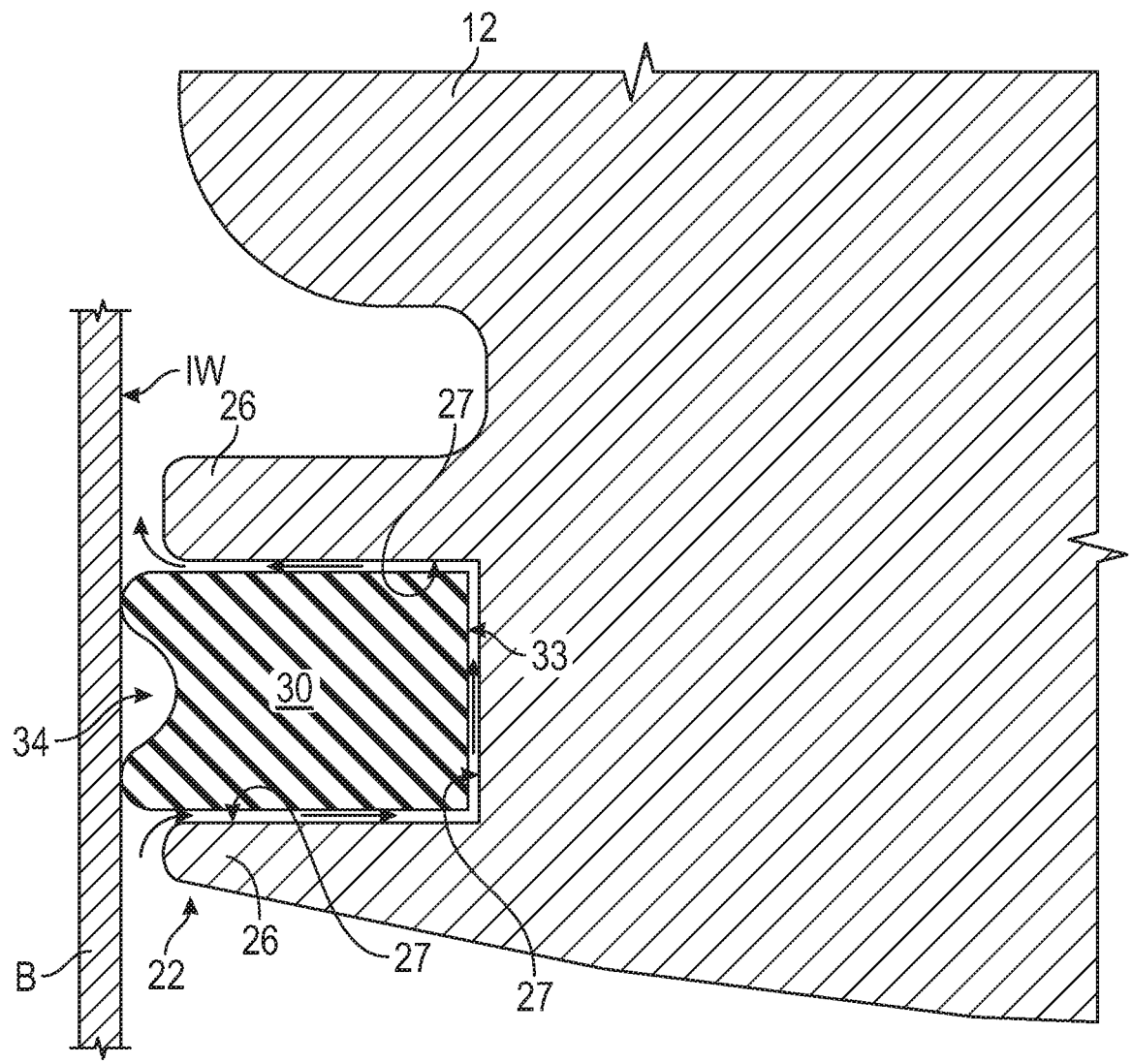
FIG. 5 shows a partial cross-sectional view of the plunger of FIG. 1 sealingly engaged with an inner surface of a syringe barrel.

According to one example embodiment, using a traditional gasket 30 without any protrusions generally provides a 0.05 mm gap between the first and second side surfaces of the gasket and at least one surface defined by the channel formed at the sealing head 22 of the plunger body 12. For example, as depicted in FIGS. 1 and 5, the sealing head 22 comprises a pair of offset or spaced-apart discs 26 defining the channel therebetween for receiving the gasket 30, and wherein inner surfaces 27 are generally spaced about 2.60 mm from each other such that a gap of about 0.05 mm is present between each inner surface 27 and side surface 44, 46 (e.g., 2.60 mm channel−2.50 mm thickness=0.10 mm gap/2=two 0.05 mm gaps). Accordingly, in some example embodiments, the 0.10 mm gap (e.g., or two 0.05 mm gaps) can be attributed to permitting a gas and/or liquid to escape from the cavity of the syringe even though the plunger is sealingly engaged with the inner wall IW of the syringe body B (see FIG. 5).

Figure 10:
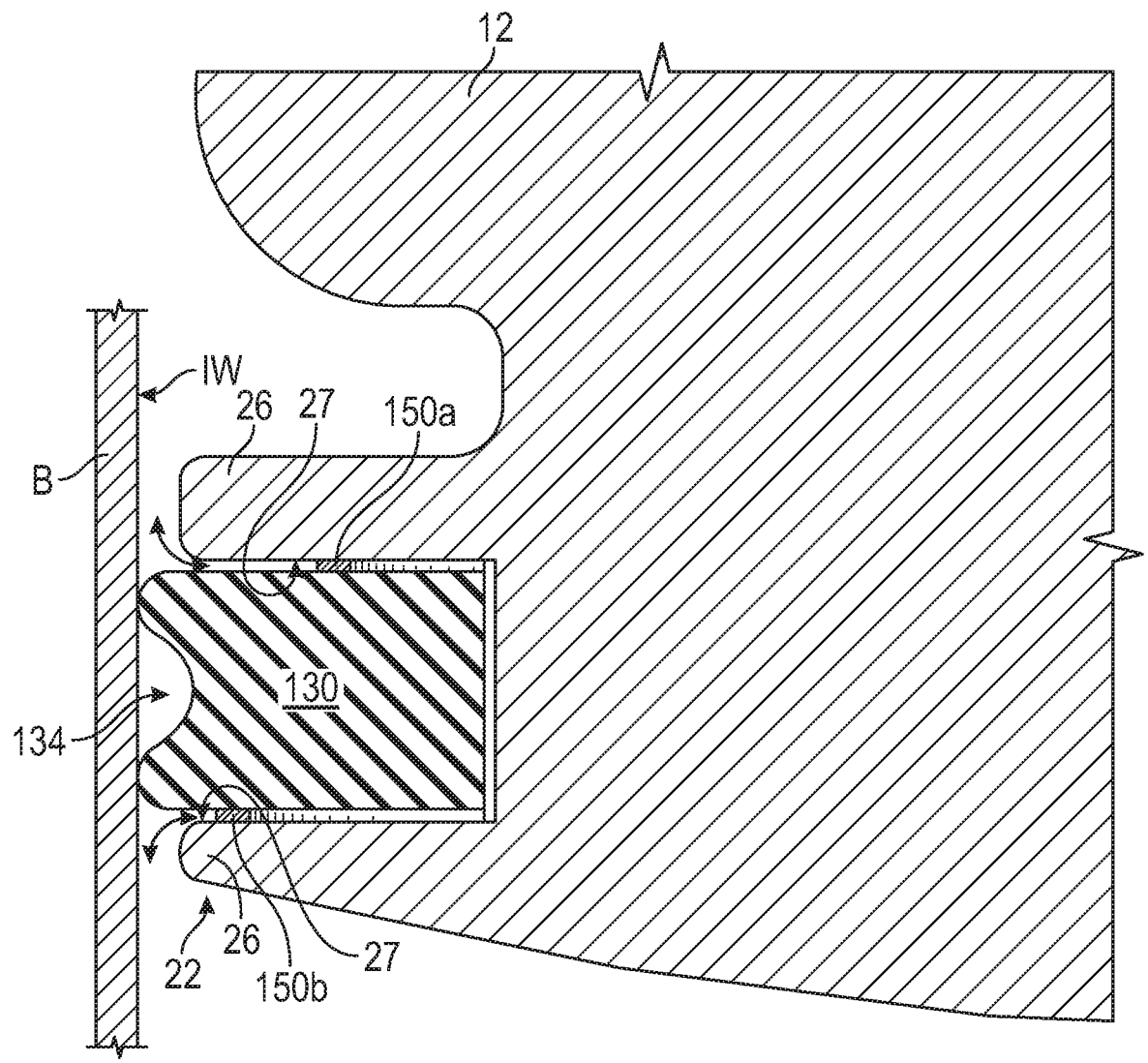
FIG. 10 is a plan view of a second side of the gasket of FIG. 9, the second side comprising surface features that are generally similar to the surface features of the first side.

In stark contrast, FIG. 10 depicts the gasket 130 comprising the surface features 150*a*, 150*b* of the first and second side surfaces 144, 146 extending outwardly from the first and second side surfaces 144, 146 and sealingly engaging the inner surfaces 27 of the spaced-apart discs 26 of the sealing head 22. As such, a gas and/or liquid is prevented from escaping the cavity of the syringe whereby the seal defined between the outer peripheral surface 134 and the inner wall IW and the seal defined between the surface features 150*a*, 150*b* and the inner surfaces 27 are substantial enough to remain sealingly engaged regardless of any pressures or other external forces that may have previously caused evaporation or fluid (e.g., gas and/or liquid) loss.

Referring back to FIGS. 6-9, the surface features 150*a*, 150*b* of the first and second side surfaces 144, 146 preferably prevent two or more of the gaskets 130 from becoming temporarily connected or stuck together after being lubricated and before being assembled with the sealing head 22 of the plunger body 12. For example, as the outermost surfaces of the surface features 150*a*, 150*b* are at least partially raised or spaced-apart from the first and second side surfaces 144, 146, the contact surface area (e.g., outermost surface of the surface features 150*a*, 150*b*) of the first and second side surfaces 144, 146 is substantially reduced to eliminate any cohesion between two or more gaskets 130. According to one example embodiment, the contact surface area or area defined by the outermost surfaces of the surface features 150*a*, 150*b* is between about $1/16$–$1/128$ the area defined by the first and second side surfaces 144, 146. Thus, with the reduction in the available contact surface area, unintentional engagement or sticking together of two or more gaskets is substantially reduced if not entirely eliminated. Accordingly, whether a plurality of gaskets 130 are contained in a hopper, carousel, bowl feeder or other automated assembly machine (e.g., to facilitate assembly of the plunger), the surface features 150*a*, 150*b* preferably prevent any such unintentional engagement or sticking together of two or more gaskets 130. Furthermore, as described above, the surface features 150*a*, 150*b* preferably provide additional sealing benefits such that evaporation or loss of a gas and/or liquid contained within the cavity of the syringe is substantially reduced if not entirely eliminated.

Figure 11:
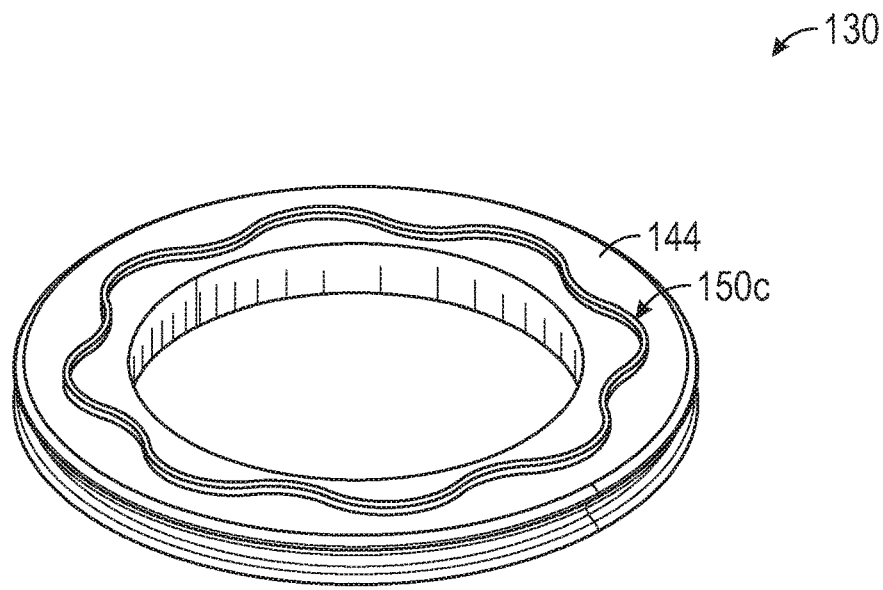
FIG. 11 is a perspective view of a first side of a gasket according to another example embodiment of the present invention, the first side comprising surface features.
Figure 12:
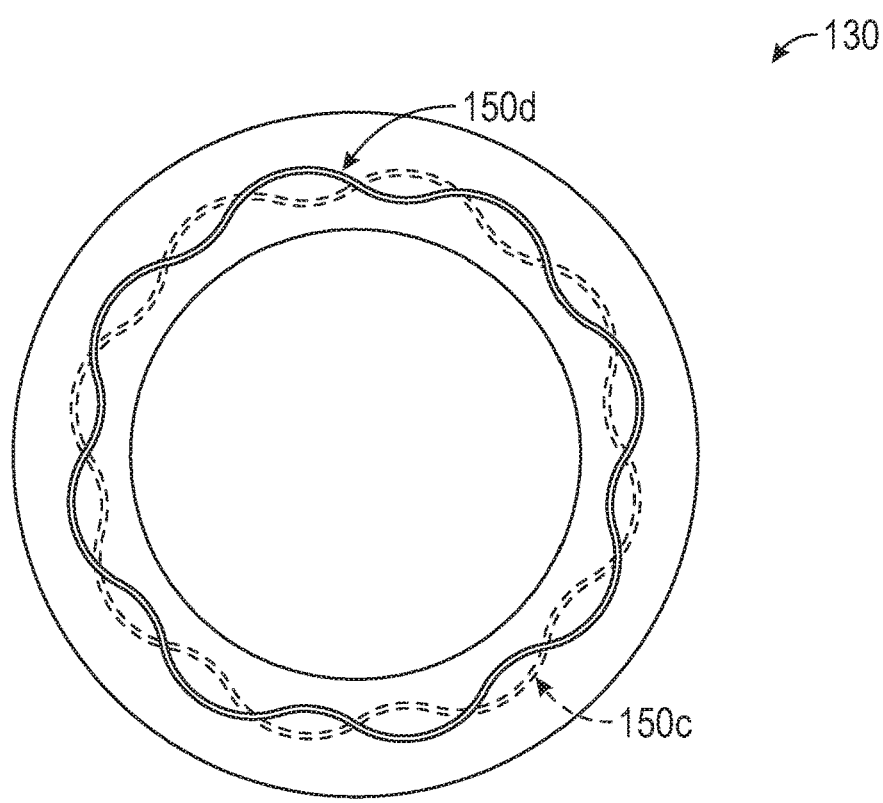
FIG. 12 is a plan view of a second side of the gasket of FIG. 11, the second side comprising surface features that are generally different to the surface features of the first side.

FIGS. 11-12 show the gasket 130 comprising alternative first and second surface features 150*c*, 150*d*, for example, which define a generally similar continuous undulating profile having peaks and valleys (or inwardly and outwardly directed lobes) alternating back and forth, inside and outside of a generally circular or otherwise configured closed path extending along the first and second side surfaces 144, 146. In example embodiments, the surface features 150*c*, 150*d* comprise continuous rib-like projections that define a plurality of peaks and valleys about their circular path along the first and second side surfaces 144, 146. As similarly described above, the surface features 150*c*, 150*d* are integrally connected to the first and second side surfaces 144, 146. Optionally, according to one example embodiment, at least one of the surface features as described herein can be a separate component that is generally connected with one or more of the first and second side surfaces 144, 146. As depicted in FIG. 12 according to one example embodiment, the surface features 150*c*, 150*d* are arranged on respective side surfaces 144, 146 in an alternating manner, for example, such that a peak portion of the surface feature 150*d* of the second side surface 146 is generally aligned with a valley portion of the surface feature 150*c* of the first side surface 144.

According to example embodiments, the circular path of the surface features 150*c*, 150*d* is generally positioned at about a midpoint between the outer peripheral surface 134 and the inner surface 133. Thus, the average diameter of the circular path of the surface features 150*c*, 150*d* is generally the average of the outer and inner diameters OD, ID of the gasket 130. For example, according to one example embodiment, the average diameter of the circular path of the surface features 150*c*, 150*d* is about 22.25 mm (e.g., (26.50 mm+18 mm)/2). In other example embodiments, the circular path of the undulating and continuous profile can comprise a desired diameter, for example, generally at least about 18 mm and generally less than about 26.50 mm.

Figure 13:
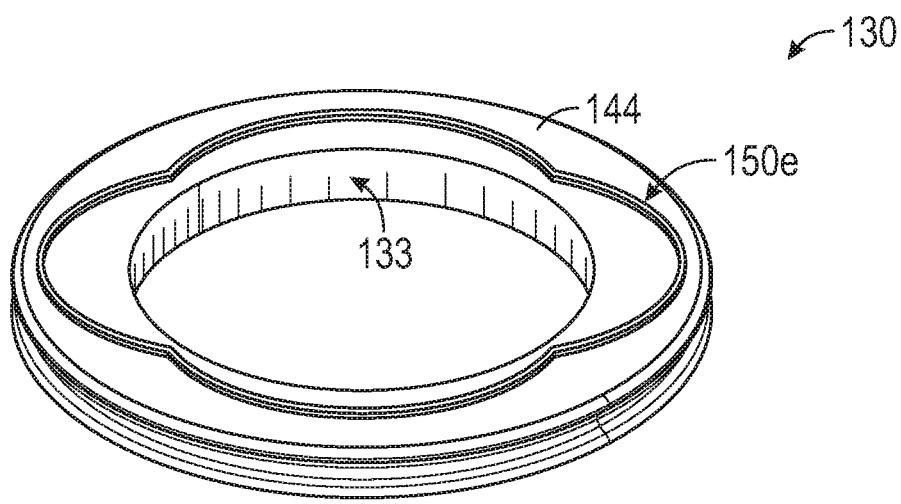
FIG. 13 shows a side cross-sectional view of a gasket according to an example embodiment of the present invention, showing the gasket having surface features formed on a first and second side thereof.
Figure 14:
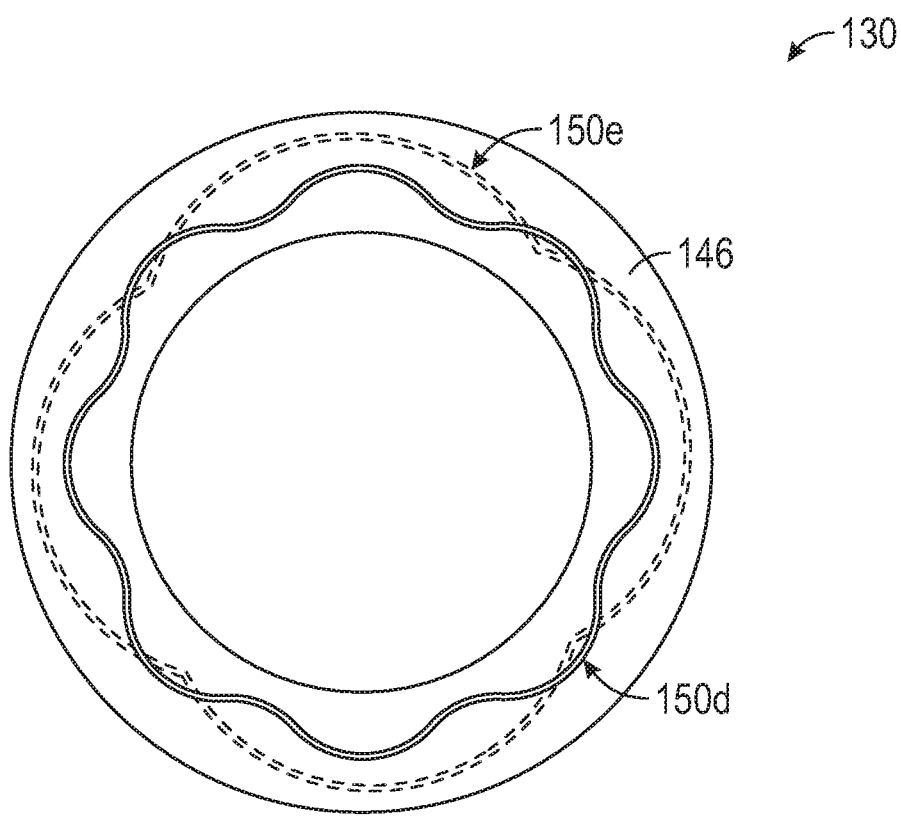
FIG. 14 shows a side cross-sectional view of a gasket according to another example embodiment of the present invention, showing the gasket having surface features formed on a first and second side thereof.

FIGS. 13-14 show the gasket 130 comprising alternative first and second surface features 150*d*, 150*e*, for example, which define generally dissimilar continuous profiles extending on the first and second side surfaces 144, 146 along a circular path. In example embodiments, the surface features 150*d*, 150*e* comprise continuous rib-like projections that generally extend on the first and second side surfaces 144, 146 along a circular path. As depicted, the first side surface 144 comprises a surface feature 150*e* and the second side surface 146 comprises the surface feature 150*d* (as described above). In example embodiments, the surface feature 150*e* defines a generally uniform profile comprising four larger radius curved paths that are interconnected at four inwardly-positioned intersections. As similarly described above, the surface features 150*e*, 150*d* are integrally connected to the first and second side surfaces 144, 146. Optionally, according to one example embodiment, at least one of the surface features as described herein can be a separate component that is generally connected with one or more of the first and second side surfaces 144, 146. As depicted in FIG. 14, a substantially minimal surface area of the surface features 150*e* of the first side surface 144 of a first gasket 130 is capable of contacting the surface features 150*d* of the second side surface 146. Accordingly, because of the disruption of the first and second side surfaces 144, 146 (e.g., by providing the protruding surface features 150*e*, 150*d*), only a substantially small surface area of one of the first and second side surfaces 144, 146 of a first gasket 130 is capable of contacting the substantially small surface area of either of the surface features 150*e*, 150*d* of another gasket 130.

As described above, the contact surface area or area defined by the outermost surfaces of the surface features 150*a*-*e* is between about $1/16$th–$1/256$th the area defined by the first and second side surfaces 144, 146. Furthermore, as depicted in FIGS. 12 and 14, the actual area of the surface features 150*a*-*e* in contact with each other can be substantially less than the total area defined by the outermost surfaces of the surface features 150*a*-*e*. For example, according to one example embodiment, the actual area of the outermost surface of one of the surface features 150*a*-*e* of a first gasket 130 in contact with the outermost surface of another of the surface features 150*a*-*e* of another gasket 130 can be between about 1-100%. According to example embodiments, when the gaskets 130 are generally arranged to be concentric relative to each other, an outermost surface of one of the surface features 150*a*-*e* will contact an outermost surface of another one of the surface features 150*a*-*e*.

In one example embodiment, when the surface features 150*a-e* of a first gasket are substantially similar to the surface features 150*a-e* of another gasket, it could be likely that substantially all of the outermost surface of one of the surface features 150*a-e* contacts substantially all of the outermost surface of another surface feature 150*a-e*. Indeed, even when the entire area of the outermost surfaces of the surface features 150*a-e* contact each other, a cohesive force (if present) applied over the available contact area is insufficient to cause two or more of the gaskets to removably engage or stick to each other, for example, even when the gaskets undergo a lubrication bath where the residual lubrication (e.g., silicone) or an outer film layer of lubrication is present on the outermost surfaces of the surface features 150*a-e*. Furthermore, according to other example embodiments, only a portion of the outermost surface of one of the surface features 150*a-e* contacts only a portion of the outermost surface of another surface feature 150*a-e* (e.g., see surface features 150*c-e* of FIGS. 12 and 14 where intersections occur). Thus, according to example embodiments, in some cases only a small percentage of the outermost area of the surface features 150*a-e* actually contact each other, thereby further reducing the contact area and potential that two or more gaskets could stick together unintentionally.

Accordingly, by providing protrusions or surface features on the first and second side surfaces of the gaskets, the available contact surface area is substantially reduced so as to fall below a surface area where cohesion could cause engagement or sticking together of two or more gaskets. For example, as described above, the outermost surface area of each surface features 150*a-e* is between about $\frac{1}{16}$th-$\frac{1}{256}$th the total surface area of each of the first and second side surfaces 144, 146. Thus, due to a substantial reduction in the available contactable surface area of the first and second side surfaces 144, 146, cohesion between two or more gaskets 130 is eliminated.

Figure 15:
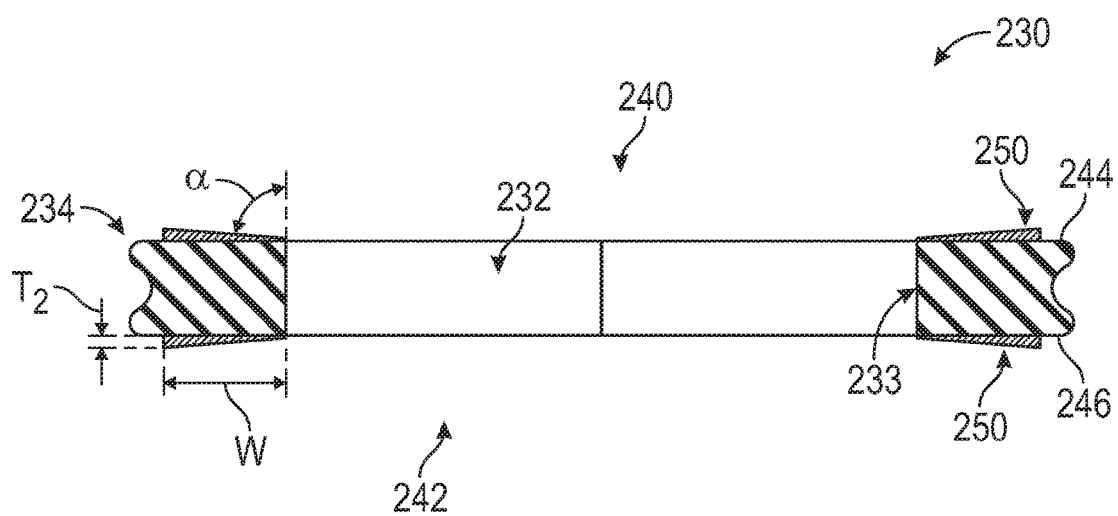
FIG. 15 shows a partial cross-sectional view of the plunger and gasket of the present invention sealingly engaged with an inner surface of a syringe barrel.

FIG. 15 shows a cross-sectional view of a gasket 230 according to another example embodiment of the present invention. As depicted, the gasket 230 is generally similar to the gasket 130 as described above. For example, the gasket comprises a thickness, an outer diameter, an inner diameter, central opening 232, a first side 240, a second side 242, an outer peripheral surface 234, a first side surface 244, and a second side surface 246. According to example embodiments, surface features 250 are provided on both the first and second side surfaces 244, 246. In example embodiments, the surface features 250 generally define a continuous and wedge-like protrusion that extends along a circular path around the entirety of the gasket. In example embodiments, the surface features 250 define a width W that is generally measured from an inner surface 233 (defining the opening 232) to an outer end thereof. In example embodiments, the outermost surface of the surface features 250 is angled relative to the first and second side surfaces 244, 246, for example, rather than being generally parallel or planar relative to the first and second side surfaces 244, 246 (as depicted in FIGS. 6-14).

According to one example embodiment, the outermost surface of the surface features 250 define an angle α that is taken from a vertical axis. According to one example embodiment, the width W is about 6.50 mm and the angle α is 85 degrees. Optionally, the width W and angle α can be chosen as desired. Furthermore, the surface features 250 define a thickness T2 where the maximum dimension is provided near the outermost portion thereof. According to one example embodiment, the thickness T2 is about 0.25 mm. Optionally, the thickness T2 can be between about 0.01 mm-0.75 mm according to some example embodiments.

According to some example embodiments, the orientation of the surface features 250 is such that the maximum dimension thereof (e.g., defined by T2) remains outside or is positioned at a diameter that is greater than a diameter of the minimum dimension of the surface features 250. For example, as depicted the minimum dimension is generally positioned substantially close to the inner surface 233 of the central opening 232 and the maximum dimension is positioned to be outside the inner surface 233 of the central opening 232 and generally closer to the outer peripheral surface 234. As such, during installation of the gasket within the channel of the sealing head 22, there is substantially zero chance that the surface features 250 would cause a disruption to the assembly thereof (e.g., a portion of the surface features 250 catching with a portion of the sealing head).

According to another example embodiment, the surface features of the first and second side surfaces can preferably be configured as desired. As described above, the surface features can be continuous, discontinuous, integral with the first and second side surfaces or separate components for attachment to the first and second side surfaces. In some example embodiments as described above, the outermost contact surfaces of the surface features can be generally planar and parallel relative to the first and second side surfaces. In other example embodiments as described above, the outermost contact surfaces of the surface features can be generally planar and angled relative to the first and second side surfaces. According to other example embodiments, the surface features of the first and second side surfaces can be configured to comprise multiple contact points, for example, which can be in the form of one or more planar surfaces (parallel and/or angled relative to the side surfaces), one or more curved surfaces, one or more desired non-linear profiles and/or a combination thereof.

According to another example embodiment, the present invention relates to method of making and assembling multiple syringe plungers. In example embodiments, the method comprises providing a plurality of plunger bodies, each plunger body comprising a first end and a second end, the first end comprising a pressure plate and the second end comprising a sealing head, the sealing head comprising a channel bound by inner surfaces; providing a plurality of gaskets for automated assembly with the channel of the sealing head, each gasket comprising a circular body comprising an outer diameter, a central opening defining an inner diameter, a first side defining a first side surface, a second side defining a second side surface, a thickness, and at least one projection outwardly extending from the first and second side surfaces, wherein a contact surface is defined at outermost portions of the at least one projection of the first and second side surfaces; lubricating the plurality of gaskets in a silicone bath; containing the plurality of lubricated gaskets within an automated assembly mechanism, the plurality of lubricated gaskets generally freely positioned and oriented within the automated assembly mechanism, wherein the automated assembly mechanism provides for feeding each of the plurality of lubricated gaskets to be assembled with individual plunger bodies, wherein the at least one projection and contact surface thereof of the first and second side surfaces substantially reduces a contact surface area of each of the plurality of lubricated gaskets such that cohesion between one or more of the lubricated gaskets is eliminated or at least substantially reduced.

While the invention has been described with reference to example embodiments, it will be understood by those skilled in the art that a variety of modifications, additions and deletions are within the scope of the invention, as defined by the following claims.

What is claimed is:

1. A syringe plunger gasket comprising:
   a gasket body comprising an inner surface bounding a central opening, an outer peripheral surface, a first side, and a second side;
   a first side surface defined on the first side of the body and a second side surface defined on the second side of the body, the first and second side surfaces being generally smooth and offset relative to each other so as define a first thickness therebetween, wherein the first side surface comprises a first side surface area and the second side surface comprises a second side surface area; and
   at least one raised surface feature projecting outwardly from at least one of the first and second side surfaces, the at least one raised surface feature comprising an outermost contact surface, the outermost contact surface defining a raised surface area that is substantially less than the first and second side surface areas of the first and second side surfaces,
   wherein the at least one raised surface feature is spaced apart from both the inner surface and the outer peripheral surface of the gasket body, and
   wherein the at least one raised surface feature completes at least one revolution surrounding the central opening.

2. The plunger gasket of claim 1, wherein the at least one raised surface feature comprises at least one rib projecting outwardly from both the first and second side surfaces, each of the at least one ribs comprising a proximal end connected to one of the first and second side surfaces of the body, and a distal end generally outwardly offset from the first end.

3. The plunger gasket of claim 2, further comprising raised surface feature side surfaces generally defined on either side of the outermost contact surface from the first and second ends of the projections.

4. The plunger gasket of claim 3, wherein a width of between about 0.25 mm-0.50 mm is defined between the raised surface feature side surfaces.

5. The plunger gasket of claim 2, wherein a thickness of between about 0.20 mm-0.30 mm is defined between the proximal and distal ends of the ribs.

6. The plunger gasket of claim 2, wherein the ribs extend along a spiraled path.

7. The plunger gasket of claim 6, wherein the spiraled path of one of the at least one rib on the first side surface extends in a clockwise direction and wherein the spiraled path of the at least one rib on the second side surface extends in a counter-clockwise direction.

8. The plunger gasket of claim 6, wherein the spiraled path is discontinuous and comprises first and second surface feature ends, the spiraled path completing at least one revolution such that at least some overlap is provided between the first and second surface feature ends.

9. The plunger gasket of claim 2, wherein the at least one rib comprises a closed profile of alternating peaks and valleys undulating about a circular path, the circular path being continuous.

10. The plunger gasket of claim 2, in combination with a plunger body comprising a sealing head, the sealing head comprising a receiving channel defined between spaced-apart inner surfaces, the spaced-apart inner surfaces configured for sealingly engaging the outermost contact surfaces of the rib-like projections.

11. The plunger gasket of claim 1, wherein the outermost contact surface of the at least one raised surface feature comprises an area that is between $1/16^{th}$-$1/256^{th}$ the area of one of the first or second side surfaces.

12. The plunger gasket of claim 1, wherein the gasket comprises an outer diameter of between about 4.5 mm-30 mm, an inner diameter of between about 2 mm-25 mm, and a thickness of between about 0.75 mm-10.5 mm, and wherein the at least one raised surface feature comprises a width of between about 0.125 mm-10 mm and a thickness of between about 0.10 mm-0.85 mm.

13. A gasket for automated assembly with a sealing head of a plunger body, the gasket comprising:
   a generally annular body comprising an outer diameter and a central opening defining an inner diameter;
   a first side defining a first side surface;
   a second side defining a second side surface; and
   at least one projection extending outwardly from each of the first and second side surfaces, wherein a contact surface is defined at outermost portions of the at least one projection on the first and second side surfaces,
   wherein the at least one projection is spaced apart from both the central opening and an outer surface defining the outer diameter of the annular body, and
   wherein the at least one projection completes at least one revolution surrounding the central opening.

14. The gasket of claim 13, wherein the first and second side surfaces each define a substantially similar surface area, and wherein the contact surface of each of the outermost portions of the at least one projection comprises a contact surface area, the contact surface area being substantially less than the surface areas of the first and second side surfaces.

15. The gasket of claim 14, wherein the at least one projection extending from the first and second side surfaces substantially reduces the available surface contact of two or more grouped-together gaskets such that unintentional cohesion of the two or more gaskets is at least substantially reduced.

16. The gasket of claim 13, wherein each of the at least one projections comprises a generally rectangular cross section defining a proximal end connected with the first and second side surfaces, and a distal end spaced outwardly from the first end and defining the contact surface.

17. A method of fabricating at least one gasket comprising:
   providing a mold comprising one or more cavities; and
   injecting a material within the one or more cavities of the mold to form one or more gaskets, each of the one or more gaskets comprising a gasket body comprising a first side and a second side, a first side surface provided on the first side and a second side surface provided on the second side, and at least one raised surface feature formed on the first and second side surfaces,
   wherein the at least one raised surface feature is spaced apart from both an inner surface extending between the first side and second side and an outer peripheral surface of the gasket body extending between the first side and second side, and
   wherein the at least one raised surface feature completes at least one revolution surrounding a central opening of the gasket that extends between the first side and the second side.

18. The method of claim 17, further comprising lubricating the one or more gaskets.

19. The method of claim 18, further comprising containing the one or more lubricated gaskets within an automated assembly mechanism, the one or more lubricated gaskets generally freely positioned and oriented within the automated assembly mechanism, wherein the at least one raised surface feature of the first and second side surfaces substantially reduces a contact surface area of each of the plurality of lubricated gaskets such that cohesion between one or more of the lubricated gaskets is substantially reduced.

20. The method of claim 19, further comprising installing each of the one or more gaskets on respective syringe plungers.

21. A method of making and assembling multiple syringe plungers, the method comprising:
providing a plurality of plunger bodies, each plunger body comprising a first end and a second end, the first end comprising a pressure plate and the second end comprising a sealing head, the sealing head comprising a channel bound by inner surfaces;
providing a plurality of gaskets for automated assembly with the channel of the sealing head, each gasket comprising a circular body comprising an outer diameter, a central opening defining an inner diameter, a first side defining a first side surface, a second side defining a second side surface, a thickness, and at least one projection outwardly extending from the first and second side surfaces, wherein a contact surface is defined at outermost portions of the at least one projection of the first and second side surfaces, wherein the at least one projection is spaced apart from both the inner diameter and an outer surface defining the outer diameter of the circular body, and wherein the at least one projection completes at least one revolution surrounding the central opening;
lubricating the plurality of gaskets in a silicone bath;
containing the plurality of lubricated gaskets within an automated assembly mechanism, the plurality of lubricated gaskets generally freely positioned and oriented within the automated assembly mechanism, wherein the automated assembly mechanism provides for feeding each of the plurality of lubricated gaskets to be assembled with individual plunger bodies,
wherein the at least one projection and contact surface thereof of the first and second side surfaces substantially reduces a contact surface area of each of the plurality of lubricated gaskets such that cohesion between one or more of the lubricated gaskets is eliminated.

22. The method of claim 21, further comprising attaching a lubricated gasket on the sealing head of the plunger body to form an assembled plunger, the lubricated gasket configured for fitting within the channel of the sealing head.

23. The method of claim 22, further comprising assembling the assembled plunger with a syringe body.

24. The method of claim 23, wherein the contact surface of the at least one projection of the first and second side surfaces is configured for sealing against the inner surfaces of the channel of the sealing head.

* * * * *